United States Patent [19]

Wolfangel

[11] 4,048,296

[45] Sept. 13, 1977

[54] RADIOPHARMACEUTICAL SCANNING AGENTS

[75] Inventor: Robert George Wolfangel, Ballwin, Mo.

[73] Assignee: Mallinckrodt, Inc., St. Louis County, Mo.

[21] Appl. No.: 581,315

[22] Filed: May 27, 1975

[51] Int. Cl.² ............. A61K 29/00; A61K 43/00; G01T 1/161

[52] U.S. Cl. ............... 424/1; 252/301.1 R; 252/313 R; 424/9

[58] Field of Search ......... 252/301.1 R, 313 R; 424/1; 250/303; 128/2 A

[56] References Cited

U.S. PATENT DOCUMENTS

| | | | |
|---|---|---|---|
| 3,683,066 | 8/1972 | Ascanio et al. | 424/1 |
| 3,720,761 | 3/1973 | Hunter, Jr. | 424/1 |
| 3,723,612 | 3/1973 | Mikheev et al. | 424/1 |
| 3,810,976 | 5/1974 | Ficken et al. | 424/1 |

OTHER PUBLICATIONS

Cragin et al., Journal of Nuclear Medicine, vol. 10, No. 10, 1969, pp. 621-623.
Garzon et al., International Journal of Applied Radiation and Isotopes, vol. 16, 1965, p. 613.
Ficken et al., Nuclear Science Abstracts, vol. 25, No. 11, June 15, 1971, p. 2403, abstract No. 24232.

*Primary Examiner*—Benjamin R. Padgett
*Assistant Examiner*—Christine M. Nucker
*Attorney, Agent, or Firm*—R. J. Klostermann

[57] ABSTRACT

Dispersions useful in preparing radiopharmaceutical scanning agents.

20 Claims, No Drawings

RADIOPHARMACEUTICAL SCANNING AGENTS

BACKGROUND OF THE INVENTION

1. Field of the Invention

This invention is directed to dispersions useful in preparing radiopharmaceutical scanning agents, to technetium labelled dispersions to methods for preparing such dispersions and to their use as scanning agents.

2. Description of the Prior Art

Technetium-99m sulfur colloids are used as scintillation scanning agents to image the reticuloendothelial system particularly the liver and spleen. They are ideal scanning agents for determining size, shape and anatomical position of the liver. Sulfur colloid particles are phagocytized by the Kupffer cells of the liver. Unlike radiopharmaceuticals which are rapidly excreted by the liver, the phagocytized sulfur colloid particles remain fixed by the Kupffer cells during the scanning period and lend to more technically uniform liver imaging. Areas of the liver scan demonstrating filling defects (reduced radioactivity) suggest the possibility of hepatic anomalies. It is possible through scanning to follow a therapeutic regimen of a diagnosed hepatic lesion.

As in the liver, sulfur colloids are phagocytized by the reticuloendothelial cells of the spleen. The imaging of the spleen has proved to be of clinical importance particularly in detection of splenomegaly. This accumulation in the spleen is of clinical value because splenomegaly is often accompanied by or is a result of hepatomegaly. Like the liver, splenic scanning can be used as a follow-up to show the results of therapeutic regimens.

Known methods for preparing technetium sulfur colloids have been practiced widely for many years. Traditionally they have been prepared extemporaneously by bubbling hydrogen sulfide through an acidified solution of sodium pertechnetate and then raising the pH from 5 to 7. Partly because of the toxicity of unreacted hydrogen sulfide and secondly to enable preparation of technetium sulfur colloid from commercial kits a second extemporaneous preparation was devised. In this preparation sodium pertechnetate injection, acidified with a mineral acid, is added to sodium thiosulfate and the solution heated. A technetium sulfur colloid is formed which is buffered to 5 to 7 and stabilized with gelatin. However, commercial kits utilizing this procedure, as is described in U.S. Pat. No. 3,683,066, requires the technician to carry out a number of steps as well as to use three separate reaction vials. Other technetium sulfur colloid procedures are described in U.S. Pat. No. 3,810,976 and 3,720,761.

While these procedures may be useful for clinical use, their usefulness is somewhat limited because such methods are time consuming and/or require a large number of procedural operations on the part of the technician which may introduce errors and affect the accuracy of the product. Thus commercially available kits typically contain a plurality of reagents and their clinical use requires the technician to perform many time consuming operations in preparing the reagents.

Consequently a pharmaceutical preparation that may be rapidly radio labelled with fewer procedural operations on the part of the technician would be an advancement in the art.

BRIEF DESCRIPTION OF THE INVENTION

In accordance with this invention a dispersion is provided which requires only the addition of a radionuclide to form a radiolabelled dispersion suitable for injection as a scanning agent. It comprises a stannous sulfur colloid dispersed in an aqueous buffer solution.

As can be seen such a reagent is safer, more reliable, and easier to use. The colloid may be prepared faster as multiple additions of several different reagents are obviated. Heating is not required nor is toxic hydrogen sulfide gas utilized.

Another aspect of this invention is directed to the technetium labelled dispersion.

Another aspect of this invention is directed to preparation of the novel dispersion and labelled dispersion as well as to the use of the labelled dispersion as a scanning agent.

DETAILED DESCRIPTION OF THE INVENTION

The first step in a preferred method of this invention comprises forming a sulfur colloid by liberating sulfur from a pharmaceutically acceptable thiosulfate by means of a pharmaceutically acceptable acid. Suitable thiosulfates include alkali metal thiosulfates, specifically, sodium, potassium or lithium thiosulfate. Ammonium thiosulfate may also be employed. It is preferred to use sodium thiosulfate because of ease and convenience.

Suitable acids that may be used in this step include any pharmaceutically acceptable acid which will cause the liberation of sulfur from the thiosulfate. Such acids include hydrochloric, sulfuric, phosphoric or nitric. Hydrochloric or sulfuric are preferred. The acid is used in an amount to effect liberation of the sulfur from the thiosulfate. Generally, the amount of acid required to liberate the sulfur is equal to proton concentrations of $10^{-5}$ M, however, it is preferred to use an excess of the stoichiometric amount required.

Those skilled in the art know how to control the reaction conditions such as reagent concentration, reagent addition and temperature to insure the satisfactory formulation of the sulfur colloid.

In the next step a stannous salt is interacted with the sulfur colloid and thiosulfate degradation products to form a stannous sulfur colloid. Any pharmaceutically acceptable stannous salt may be utilized such as stannous halides, specifically stannous chloride, stannous iodide, stannous bromide, stannous flouride. Also other pharmaceutically acceptable stannous salts such as stannous hydrate, stannous sulfate, stannous nitrite, stannous hydroxide, stannous oxide, stannous sulfide, stannous hydride, stannous sulfate or stannous phosphate may be used. Generally 0.1 mole to 1 mole of stannous salt is employed for each mole of the thiosulfate salt.

In the next step a buffer is added. Suitable aqueous buffer solutions to buffer the reaction mixture to a pH of 3 - 4 are known to those persons skilled in the art. For example a buffer solution utilizing glycine and sodium hydroxide could be employed. Alternatively, a buffer utilizing sodium acetate, and acetic acid or a buffer of sodium biphosphate and sodium hydroxide can be utilized. Other buffers are described in *Remington's Practice of Pharmacy*, Eleventh edition, which is incorporated herein by reference, particularly on pages 170 and 171.

It is preferred as a next step to add a stabilizing agent to protect the chemical and physical properties of the colloidal particles. The stabilizer functions to stabilize the particles in the aqueous buffer solution and to protect their physical and chemical properties during their normal shelf life or aging.

Such stabilizing agents that may be used in the process of this invention include any pharmaceutically acceptable material that will stabilize the stannous sulfur colloid in the aqueous buffer soluton and/or effectively reduce degradation during lyophilization and aging and storage thereafter. These include carbohydrates, organic acids, amino acids alcohols or mixtures thereof.

Illustrative carbohydrates include sugars such as monosaccharides and disaccharides and non-sugars illustrated by polysaccharides. Monosaccharides are those sugars containing 3 or more carbon atoms that cannot be split up any further by hydrolysis. Disaccharides are those sugars that split up under the influence of hydrolysis into two molecules of monosaccharides. The polysaccharides include those sugars which upon hydrolysis yield 3, 4 or more monosaccharides and a large number of related substances which bear a close chemical relationship to sugars since by hydrolytic change they can be converted into many molecules of glucose or other monosaccharides.

Specific examples of monosaccharides include trioses, tetroses, pentoses, hexoses. More specific examples include glycerose, erythrose, threose, arabinose, xylose, ribose, lyxose, dextrose, levulose, sorbose, galactose, mannose, etc. Specific examples of disaccharides include sucrose, lactose, maltose, isomaltose, trehalose, cellobiose, gentiobiose, melibiose, glucoxylose, primeverose, vicianos, etc.

Classes of polysaccharides include trisaccharides, tetrasaccharides, starches, gums, celluloses, etc. Specific examples include raffinose, gentianose, melezitose, stachyose, dextrins, insulin, glycogen, galatosan, mannosa, antural gums, pentosans, mucilages, and pectin compounds.

Preferred sugars include dextrose and lactose.

Other examples of carbohydrates may be found in *Remington's Practice of Pharmacy*, Eleventh Editon, pages 1019-1032, which is incorporated herein by reference.

All pharmaceutically accepted organic acids and salts thereof may be used in the practice of this invention. Monocarboxylic acids are chracterized by the formula RCOOH where R is an aliphatic, alicyclic, or aromatic group. Aliphatic acids include those containing 1 to 30, preferably 1 to 10, carbon atoms such as formic, acetic, propionic, butyric, valeric, sorbic, caproic, enanthic, caprylic, pelargonic, carpic, lauric, myristic, palmitic, and stearic acids. Branched chain organic acids may also be employed such as isobutyric acid or isolauric acid. Dicarboxylic acids, containing up to 20, preferably 2 to 10, carbon atoms, may also be employed, for example, oxalic acid, malonic acid, succinic acid, glutaric acid, ascorbic acid, adipic acid, pimelic acid, suberic acid, azelaic acid, sebacic acid, etc. Tricaboxylic acids containing up to 20 carbon atoms, preferably 3 to 10 carbon atoms, may be used such as citric acid.

It is preferred to use citric, ascorbic, glutaric or succinic acid.

Amino acids that may be used include aliphatic amino acids, aromatic amino acids, sulfur containing amino acids, heterocyclic amino acids, etc. Specific examples include glycine, alanine, serine, threonine, valine, leucine, isoleucine, phenylalanine, tyrosine, cysteine, cystine, methionine, tryptophan, proline, hydroxyproline, aspartic acid, glutamic acid, histidine, lysine, arginine, etc. Glycine is preferred.

Other examples may be found in *Remington's Practice of Pharmacy*, Eleventh Edition, Pages 929 to 939 which is incorporated herein by reference.

All pharmaceutically accepted aliphatic or aromatic mono or poly alcohols containing 6 or more carbon atoms, preferably 6 to 12, may also be used. These include sorbitol, mannitol, etc.

Polyvinylpyrrolidone may also be used.

The amount of stabilizing agent used in the practice of this invention can be readily determined by those skilled in the art. Generally it will be an amount to effectively stabilize the stannous sulfur colloidal particles in the aqueous buffer solution, and to reduce the degradation of the physical and chemical properties during lyophilization and normal storage thereafter. Usually this is an amount of from 1 to 800 times by weight of the dispersion, preferably 10 to 650 times. For example in the case of organic acids such as citric acid and succinic acid, an amount of about 10 times to about 400 times the amount by weight of the stannous sulfur colloid is used.

In the case of carbohydrates such as lactose an amount of about 5 times to about 500 times the weight of the dispersions of stannous sulfur colloidal particles is used.

In the case of amino acids such as glycine an amount of about 10 times to 600 times the weight of the dispersion of stannous sulfur colloidal particles is used.

Amino acids such as glycine and carbohydrates such as dextrose and lactose are especially preferred.

It is especially preferred to use amino acids since they function both to buffer and stabilize.

Another method for preparing the novel compositions of the present invention is to react the thiosulfate acid and stannous salt at the same time.

Generally the concentration of the dispersion of stannous sulfur colloid in the aqueous buffer solution is from about .001% to about 1.0%, preferably 0.01% to 0.1% by weight/volume, based on the total volume of the dispersion. The average particle size is from about 1 m$\mu$ to about 1$\mu$.

Following the preparation of the aqueous dispersion it is preferred to lyophilize or freeze dry the dispersion to remove the water and form a lyophilized product. Such a procedure insures stability for long periods of time. When the product is ready for use it can easily be reconstituted.

When the lyophilized product is ready to be used, it can be labelled, for example, by using pertechnetate injection obtained from any sterile generator of the nature illustrated by U.S. Pat. No. 3,369,121. In practice following sterile and antiseptic conditions and an eluate of technetium-99m obtained from a sterile technetium generator as indicated above is injected into the vial containing the lyophilized product. Although the nature of the labelling reaction has not been defined, it is generally thought that a reduction of the valence of technetium takes place with a concomitant formation of a technetium labelled colloid. The labelled dispersion is then ready for injection.

The labelled technetium sulfur colloid may be advantageously utilized in liver scanning according to well known procedures. For example after intravenous injection of a precalculated dose of about 1 to 3 millicuries of technetium-99m sulfur colloid, the patient is placed in a supine position. Before injection there is no patient preparation necessary. Scanning is begun approximately 15 minutes after the injection. Generally three scan positions are obtained, anterior, right lateral, and posterior.

Likewise the technetium-99m sulfur colloid is advantageously used in spleen scanning. For example, after intravenous administration of the technetium sulfur colloid the same general procedure used for liver scanning is employed. The scan views normally include an anterior, left lateral and a posterior position. Where an enlarged spleen is concerned an oblique view or views may be required to distinguish the liver and spleen.

The invention will now be illustrated by the following example. All parts are by weight unless otherwise indicated.

EXAMPLE 1

103 ml of 5 normal HCl is added to 15.4 ml of sodium thiosulfate $\cdot$ 5 H$_2$O (100 mg per ml). After the reaction is complete, add 92.8 ml of stannous chloride $\cdot$ 2H$_2$O (10 mg/ml). After the formation of stannous sulfur colloid, 387 ml of 1 N NaOH and 3465 ml of 2 N glycine is added as a stabilizer and a buffer to bring the pH to 3.2 – 3.5. 481 ml of water is added to bring the volume to 4544.2 ml.

The bulk dispersion is then divided into 4540 one ml vials, each vial containing the following:

| Ingredients | Milligrams per milliliter |
|---|---|
| HCl | 4.75 |
| Na$_2$S$_2$O$_3$ . 5H$_2$O | 0.34 |
| NH$_2$CH$_2$COOH | 105.0 |
| Sodium Hydroxide | 3.42 |
| SnCl$_2$ . 2H$_2$O | 0.204 |

The particle size of the colloid is less than about 1 micron in diameter. There is theoretically about $4 \times 10^7$ sulfur particles per ml of sulfur colloid solution.

Each vial is placed in a vacuum sublimator and the product temperature reduced until freezing has occurred. The sublimator is evacuated and then the product is maintained under vacuum until a stable product temperature of about 0° C. is obtained (about 16 hours). When ready for use the vials are reconstituted and labelled with pertechnetate using the eluate of technetium-99m as obtaind from a technetium generator.

EXAMPLE 2

Tc-99m labelled - sulfur colloid of Example 1 dispersions is administered intravenously into laboratory animals, an amount equal to or greater than 80% of the administered radioactivity deposits within the Reticuloendothelial cells of the liver, 15% or less in the spleen and 10% or less in the bone marrow. These quantities have been ascertained by injection of test animals with the labelled colloidal dispersion, allowing 15 – 30 minutes for deposition to occur, sacrificing the animals by an overdose of general anesthetic, dissection and removal of the organs of interest and monitoring these organs for radioactivity content.

The tissue distribution determinations described above have been verified by obtaining scintigraphs of (scanning) rabbits dosed with the radioisotopically labelled Tc-99m sulfur colloid dispersion. The scintiphotos obtained clearly showed that the major organ of deposition was the liver, followed by spleen and some bone marrow.

EXAMPLE 3

Heat 10 ml 1N hydrochloric acid to about 100° C. for 1 minute, add 3.0 ml of sodium thiosulfate pentahydrate (10 mg/ml) and continue heating at 100° C. for 8 minutes. Quickly add 12.5 ml of 4M sodium acetate. Continue heating for 4 minutes, then cool to room temperature. Add 2.0 ml of stannous chloride dihydrate (6 mg/ml) dissolved in 1N hydrochloric acid, followed by 2.5 ml of 4M sodium acetate. Allow to stand undisturbed for 30 minutes at room temperature. Dilute and mix with an equal volume of water for injection. Dispense 1 ml of the dispersion in 10 ml serum vials, place in sublimator, freeze, evacuate chamber and continue sublimaton process until a stable product temperature of 0° C. is achieved and a stable vacuum reading of 20$\mu$ or less is obtained (about 18 hours).

EXAMPLE 4

10 ml of 1N hydrochloric acid is heated to about 100° C., 3 ml of sodium thiosulfate pentahydrate (10 mg/ml) added, the heating continued for 8 minutes, then 25 ml of 4M sodium acetate added. After 4 minutes additional heating, cool to room temperature, add 2 stannous chloride dihydrate (10 mg/ml) dissolved in 1N hydrochloric acid, 4 ml of 4M sodium-acetate and incubate for 30 minutes at room temperature. Dilute the product with an equal volume of 10% dextrose solution and freeze dry as in Example 3.

EXAMPLE 5

Mix 15.4 ml of sodium thiosulfate solution (100 mg/ml) and 62 ml of sterile water in 200 ml Erlenmeyer flask. With continuous stirring, 23 ml of 5N hydrochloric acid is added dropwise into the mixture within 5 minutes. This solution is then dispersed into a solution which contains 80 ml of 5N hydrochloric acid and 420 ml of sterile water. 1540 ml of buffer solution (2N glycine : 1N sodium hydroxide 14:1) is added to bring the pH to 3.2 – 3.3. Then 93 ml of stannous chloride (6 mg/ml) in 1N hydrochloric acid solution is introduced and buffered with 270 ml of buffer solution to pH = 3.2 – 3.3. The solution is allowed to equilibrate at room temperature for 1.5 hrs. under N$_2$ atmosphere.

Dispense 0.5 ml into 10 cc sterile pyrogen free U.S.P. Type 1 glass vials and partially stopper the vials. These vials are placed into lyophilizine trays and covered with sterility covers.

The trays with product vials are placed in a lyophilizer and then lyophilized until final product temperature reaches 0° C. Then the vials are stoppered completely under an atmosphere of dry 99.9% pure 0.22$\mu$ millipore filtered N$_2$. The vials are then taken from the lyophilizer and stored in th refrigerator (4° C.).

As various changes could be made in the above methods and products without departing from the scope of the invention it is intended that all matter contained in the above description is illustrative. It is to be understood, therefore, the invention is not limited except by the appended claims.

What is claimed is:

1. A dispersion useful in forming an injectable radiopharmaceutical scanning agent comprising a stannous sulfur colloid dispersed in an aqueous buffer solution.

2. A dispersion according to claim 1 wherein said dispersion is buffered to a pH of 3 to 4 at 25° C.

3. A dispersion according to claim 2 wherein said dispersion contains an effective amount of a stabilizing agent to stabilize said particles in said buffer solution, said dispersion having an average colloid particle size of from about 1 millimicron to about 1 micron.

4. A dispersion useful in forming an injectable radiopharmaceutical scanning agent prepared by the method comprising
   a. forming a dispersion containing a sulfur colloid by reacting in an aqueous medium a thiosulfate with a pharmaceutically acceptable acid,
   b. interacting a pharmaceutically acceptable stannous salt with the dispersion of (a) and thereafter buffering the resulting dispersion.

5. A dispersion according to claim 4 which is buffered to a pH of 3 to 4.

6. A dispersion according to claim 5 wherein said dispersion contains an effective amount of a stabilizing agent to stablize said particles of said dispersion in said buffer solution, said dispersion having an average colloid particle size of from about 1 millimicron to about 1 micron.

7. A dispersion according to claim 6 wherein said stabilizing agent is glycine.

8. An injectable radiopharmaceutical scanning agent comprising the dispersion of claim 4 labelled with technetium-99m.

9. A method for preparing a radiopharmaceutical scanning agent which comprises labelling the dispersion of claim 4 with technetium-99m.

10. method for preparing a dispersion of a stannous sulfur colloid in an aqueous buffer solution which is useful in forming an injectable radiopharmaceutical scanning agent comprising
    a. forming a dispersion containing a sulfur colloid by reacting in an aqueous medium a thiosulfate with a pharmaceutically acceptable acid,
    b. interacting a pharmaceutically acceptable stannous salt with the dispersion of (a) to form a dispersion containing a stannous sulfur colloid and buffering said dispersion contaning said stannous sulfur colloid.

11. A method according to claim 10 wherein a stabilizer is added to stabilize said stannous sulfur colloid particles.

12. A method according to claim 11 wherein said stabilizer is glycine.

13. A method according to claim 12 wherein said dispersion is labelled with technetium-99m.

14. A method according to claim 11 wherein said thiosulate is sodium thiosuflate said stannous salt is stannous chloride and said acid is hydrochloric.

15. An injectable radiopharmaceutical scanning agent comprising a technetium-99m labelled sulfur colloid to which stannous ions are attached dispersed in an aqueous buffer solution.

16. A scanning agent according to claim 8 wherein said dispersion contains an effective amount of a stabilizer to stabilize said particles in said buffer solution, has a pH of 3 to 4 and has an average particle size of from about 1 millimicron to about 1 micron.

17. A scanning agent according to claim 16 wherein said stabilizer is glycine.

18. In a method for imaging the reticuloendothelial system wherein a scintillation scanning agent is intravenously injected and thereafter a scan is made, the improvement comprising utilizing as the scintillation scanning agent the radiopharmaceutical scanning agent of claim 8.

19. In a method for imaging the reticuloendothelial system wherein a scintillation scanning agent is intravenously injected and thereafter a scan is made, the improvement comprising utilizing as the scintillation scanning agent the radipharmaceutical scanning agent of claim 16.

20. In a method for imaging the reticuloendothelial system wherein a scintillation scanning agent is intravenously injected and thereafter a scan is made, the improvement comprising utilizing as the scintillation scanning agent the radiopharmaceutical scanning agent of claim 17.

* * * * *

UNITED STATES PATENT AND TRADEMARK OFFICE
CERTIFICATE OF CORRECTION

PATENT NO. : 4,048,296
DATED : September 13, 1977
INVENTOR(S) : Robert G. Wolfangel It is certified that error appears in the above-identified patent and that said Letters Patent are hereby corrected as shown below:

Col. 2, line 47, "flouride" should read -- fluoride --
Col. 2, line 52, "the" should be added before -- stannous --
Col. 3, line 32, "vicianos" should read -- vicianose --
Col. 3, line 36, "antural" should read -- natural --
Col. 3, line 46, "chracterized" should read -- characterized --
Col. 4, line 25, "dispersions" should read -- dispersion --
Col. 5, line 46, "obtaind" should read -- obtained --
Col. 5, lines 50-51, "dispersions" should read
   -- dispersion --
Col. 6, line 15, "sublimaton" should read -- sublimation --
Col. 6, line 24, "2" should read -- 2 ml --
Col. 6, line 63, Claim 1, "stannous" should be deleted
Col. 6, line 64, Claim 1, "to which stannous ions are
   attached" should be inserted after -- colloid --

UNITED STATES PATENT AND TRADEMARK OFFICE
CERTIFICATE OF CORRECTION

PATENT NO. : 4,048,296

DATED : September 13, 1977

INVENTOR(S) : Robert G. Wolfangel

It is certified that error appears in the above–identified patent and that said Letters Patent are hereby corrected as shown below:

Col. 8, line 9, Claim 14, "thiosulate" should read -- thiosulfate --

Col. 8, line 9, Claim 14, "thiosuflate" should read -- thiosulfate --

Col. 8, line 32, Claim 19, "radipharmaceutical" should read -- radiopharmaceutical --

Signed and Sealed this

Seventh Day of February 1978

[SEAL]

Attest:

RUTH C. MASON
Attesting Officer

LUTRELLE F. PARKER
Acting Commissioner of Patents and Trademarks